United States Patent [19]

Proffitt et al.

[11] Patent Number: 5,415,024

[45] Date of Patent: May 16, 1995

[54] COMPOSITION ANALYZER FOR DETERMINING COMPOSITION OF MULTIPHASE MULTICOMPONENT FLUID MIXTURE

[75] Inventors: Arthur C. Proffitt, Cody, Wyo.; William C. Barron, Sugarland, Tex.

[73] Assignee: Marathon Oil Company, Findlay, Ohio

[21] Appl. No.: 991,698

[22] Filed: Dec. 16, 1992

[51] Int. Cl.$^6$ .............. G01F 1/74; G01K 17/20; G01N 25/00

[52] U.S. Cl. .................. 73/61.44; 73/61.46; 73/61.76; 73/861.04; 374/32; 374/33; 374/41; 374/54; 392/478

[58] Field of Search ........... 73/61.59, 61.44, 61.46, 73/61.74, 61.76, 861.04; 374/32, 33, 40, 41, 45, 54; 392/478

[56] References Cited

U.S. PATENT DOCUMENTS

| | | | |
|---|---|---|---|
| 3,766,357 | 10/1973 | Koester, Jr. | 392/478 |
| 3,898,882 | 8/1975 | Prokopius | 73/861.04 |
| 4,233,494 | 11/1980 | Paulik et al. | 392/478 |
| 4,751,842 | 6/1988 | Ekrann et al. | 73/61.44 |
| 4,813,270 | 3/1989 | Baillie | 73/861.04 |
| 4,815,536 | 3/1989 | Prendergast et al. | 73/61.44 |
| 4,881,412 | 11/1989 | Northedge | 73/861.04 |

OTHER PUBLICATIONS

Geankoplis, Christie J., *Transport Processes; Unit Operations*, 2nd ed., 1983, pp. 207–208, 212–213, 235.

*Primary Examiner*—Robert J. Warden
*Assistant Examiner*—L. M. Crawford

[57] ABSTRACT

A composition analyzer and a method of use for determination of the masses of individual components in a multiphase multicomponent fluid system containing a gas. Data and relationships not measured by the analyzer during operation but required by the method are predetermined or researched and stored, and other required data is instantaneously obtained from the composition analyzer during process operation. All these data are used in an iteration process to accurately determine the mass composition of each fluid component. The preferred means for adding energy to the fluid mixture in the test apparatus is comprised of an electrically conductive conduit through which the fluid mixture flows and which heats the fluid mixture when electrically energized.

5 Claims, 2 Drawing Sheets

COMPOSITION ANALYZER FOR DETERMINING COMPOSITION OF MULTIPHASE MULTICOMPONENT FLUID MIXTURE

FIELD OF THE INVENTION

This invention relates to the quantitative analysis of a multicomponent multiphase fluid. More particularly, it relates to an instrument and a method of use for determining the composition and/or individual component flow rate in a three-component fluid system containing two liquids and a gas or a liquid, a solid and a gas or two solids and a gas.

BACKGROUND OF THE INVENTION

It is often important to be able to determine the ratio of fluids in a multicomponent multiphase fluid system. For example, in the petroleum industry, fluid produced from a hydrocarbon formation commonly includes oil, water and gas. It is important to know the net oil production from a well and the volume of gas and water in the produced fluid, as this information is utilized in a variety of areas, such as, for example, in the determination of royalty payments, productivity measurements, the cost of lifting production fluid, equipment sizing and reservoir and well management.

A number of different ways of measuring oil, gas and water production rates have been suggested. A commonly used method has been to simply introduce a predetermined volume of production fluid into a three-phase separator vessel where the water settles beneath the oil and the gas rises above it, after which the individual phases are measured. This is not an entirely satisfactory method, however, because it is slow, requiring many hours and frequently days for the emulsions of oil, water and gas produced by wells to separate in the vessels. It may also be necessary to add expensive chemicals to enhance this separation. In addition, the apparatus is required to be semi-continuously operated, with data being acquired by visual and manual means, manually recorded and subsequently utilized in carrying out suitable mathematical calculations in order to obtain the information sought. The apparatus is necessarily large, expensive and cumbersome and is such that satisfactory operation requires great care and skill on the part of the technicians operating it. Also, use of such apparatus and its related method of testing production fluid for net oil content has frequently resulted in an error of plus or minus 10%, which is not acceptable by today's standards.

Other suggested methods make use of a variety of measurements and procedures to determine the flow rate and composition of multiphase fluid mixtures. There is, however, no inexpensive, reliable commercially available instrumentation for measuring oil, water and gas production rates from a producing oil well, and in particular, for accurately measuring the production rates of individual components of a multiphase fluid comprised of very large amounts of water or gas on a real time basis. While this discussion has been primarily in connection with measurement problems relating to multiphase fluid produced from a hydrocarbon formation, it is noted that similar measurement problems exist in connection with other three-component multiphase fluid systems.

It is an object of the present invention to provide a method for determining the composition of fluids in a three-component multiphase fluid system which is accurate over the entire range of the components from 0% to 100%, uses commonly understood thermodynamic and instrumentation technology, requires no chemicals for phase separation, lends itself to automation, is not space or capital intensive and provides accurate results. More specifically in connection with the petroleum industry, it is an object of the invention to provide such a method which is applicable to the determination of the composition of water, gas and oil in a multiphase system comprised of these fluids. The ability to use such a method in the field in a remote location would be of further benefit.

BRIEF SUMMARY OF THE INVENTION

In accordance with the method of the invention, a three-component multiphase fluid mixture consisting of two different liquid components, either miscible or immiscible, and a gas is caused to flow through an insulated conduit and a measured amount of energy is added to the conduit. The changes in the "in" and "out" temperatures, pressures and flow rates caused by the measured energy addition are measured as well as the inside and outside insulation temperatures and, based on a first approximation that the volume of the liquid components prior to the energy addition and the volume of the liquid components after the energy addition are essentially equal, i.e., the ratio of the liquid components approximates unity, the approximate volume of the gas in the fluid mixture is determined. The corresponding liquid volume of the fluid mixture is then calculated using the approximate volume of the gas component flowing into the conduit and a volume balance. Heat losses due to heat absorbed by the gas and heat lost through the conduit insulation are next determined.

Having measured or determined the heat gained by the gas, the heat losses, the approximate liquid volume, and the in and out temperatures, an approximation of the product of liquid density and specific heat can be calculated, from which an approximate mass composition is determined. Knowing the relationship between mass composition and the product of density and specific heat as a function of temperature allows a determination of liquid density at the in and out temperatures, from which a new ratio of the liquid volumes is calculated.

The calculation process is repeated until the last computed ratio of the liquid volumes equals the previous ratio, the last computed volume of gas entering the conduit equals the previous computed volume, and the last mass composition equals the previous mass composition. Thus the invention utilizes an iteration process having a logical starting point to determine the composition of the fluid mixture.

When adding energy to the fluid mixture, it is preferred to employ a conduit comprised of electrically conductive material having a sufficiently high resistance so as to act as a heater when relatively low voltage electrical energy is applied to it. A suitable material of construction for the conduit is a nickel/chromium/iron alloy commercially available under the name NI-CHROME. Preferably, data is collected through use of the test apparatus under conditions such that the rate of heat pick-up by the apparatus at the instant a data point is taken equals zero.

A programmable logic controller is employed to receive input from data measurements taken of the fluid mixture, to store data and relationships required by the method and to solve gas law and thermodynamic equations incorporating such data.

Although the invention is applicable to various forms of three-component multiphase fluid systems, including fluids comprised of liquids containing soluble, suspended or dispersed solids, it is of particular interest in determining the composition of fluid systems consisting of oil, water and gas.

The features of the invention which enable the composition of a multiphase fluid to be determined are brought out in more detail in the following detailed description, wherein the above and other aspects of the invention, as well as other benefits, will readily be apparent.

DETAILED DESCRIPTION OF THE PREFERRED EMBODIMENTS

Figure 1:
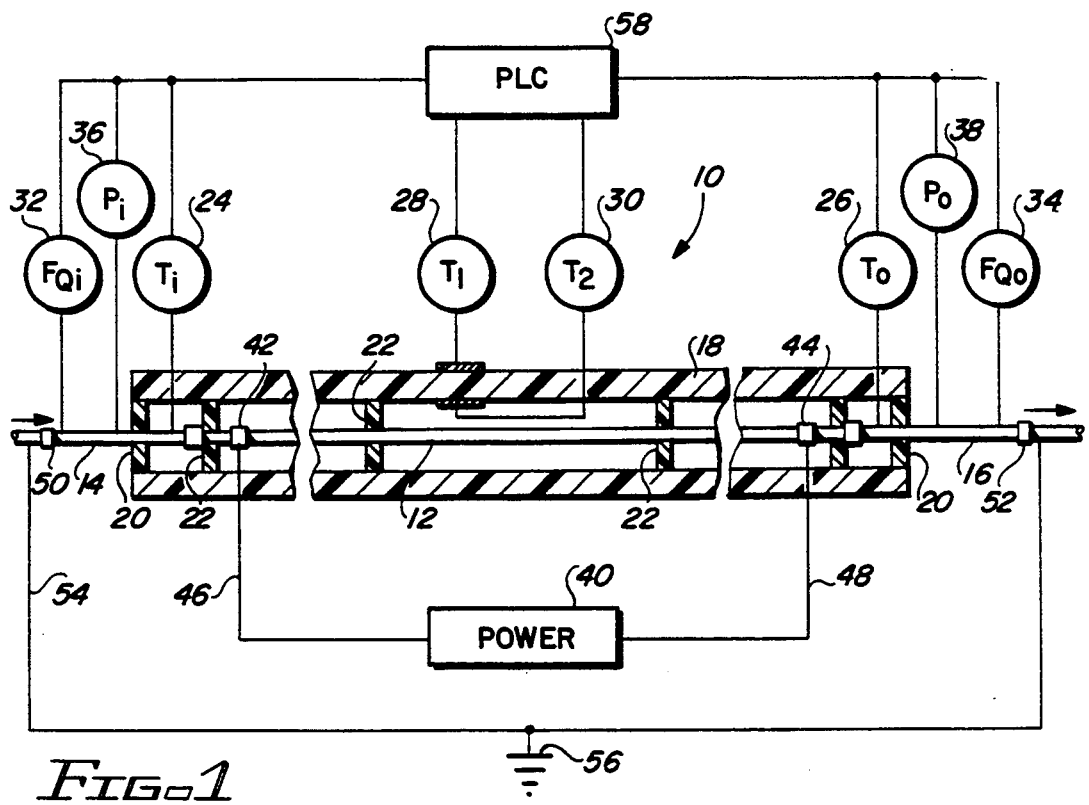
FIG. 1 of the drawing is a simplified longitudinal sectional view of the composition analyzer used in carrying out the method of the present invention.

Referring to FIG. 1 of the drawing, the test apparatus or composition analyzer 10 includes a conduit 12 which is connected at its upstream end to an inlet pipe 14 and at its downstream end to an outlet pipe 16. While the dimensions and configuration of the conduit 12 may vary according to the system and environment involved, one design which describes the invention takes the form of a NICHROME tube four feet in length, having an outside diameter of 0.180 inch and a wall thickness of 0.0015 inch. A tube or sheath of insulation 18 surrounds the NICHROME tube 12. The insulation employed in the test apparatus was STYROFOAM rigid foamed polystyrene plastic having a wall thickness of one inch and an inside diameter of the size used for insulating nominal 2-inch pipe. Plastic washers or discs 20 of the same material, which snugly surround the inlet and outlet conduits 14 and 16 and fit into the ends of the insulation tube 18, provide insulation at the ends of the tube. Similar discs 22 are provided to support the slender tube 12 at its ends and at points intermediate to the ends.

Temperature sensors 24 and 26 are provided in the inlet and outlet pipes, respectively, at points within the insulating sleeve 18 for measuring the temperature ($T_i$) of the fluid entering the conduit 12 and the temperature ($T_o$) of the fluid exiting the conduit. The sensors may take any suitable form, such as thermocouples, thermistors and resistance thermal devices. Additional temperature sensors 28 and 30 are provided at the outer and inner wall surfaces of the insulation sleeve to measure representative outside and inside temperatures, ($T_1$ and $T_2$) respectively, of the insulation. A flowmeter 32 is shown as being connected to the inlet pipe 14 to measure fluid flow ($F_{Qi}$) just upstream from the insulation 18 and a flowmeter 34 is connected to the outlet pipe 16 to measure fluid flow ($F_{Qo}$) just downstream from the insulation 18. In addition, pressure sensors 36 and 38 are connected to the inlet and outlet pipes near the flowmeters to measure the fluid pressure ($P_i$) prior to entering the apparatus and the fluid pressure ($P_o$) upon leaving the apparatus. The sensors for measuring $F_{Qi}$, $P_i$ and $T_i$ are located as close together as possible, consistent with good instrumentation practice, as are the sensors for measuring $F_{Qo}$, $P_o$ and $T_o$.

A direct or alternating current power source 40 is connected to the conduit 12 at points 42 and 44, spaced a short distance from the inlet and outlet ends, by lines 46 and 48. Preferably, the conduit 12 is electrically isolated from upstream and downstream piping with a suitable insulating material connected to the pipes 14 and 16 at 50 and 52, respectively, and an electrical shunt 54 connecting the pipes 14 and 16 is grounded, as indicated at 56. The energy input of the power source represents the heat added to the system (q), as explained in more detail below.

The apparatus described is used to measure the energy input, the heat loss from the apparatus, the temperatures in and out, the flow rates in and out and pressure changes in and out of a multiphase fluid. These values are then used to determine the composition of the multiphase fluid through application of the ideal gas laws or some modification thereof and thermodynamic principles. As stated previously, the invention makes use of the fact that changes in temperature and pressure in a multiphase fluid produce a much greater percentage change to the gas volume than to the liquid and/or solid volume. By measuring the in and out fluid temperatures, pressures and flow rates, and inside and outside insulation temperatures as a result of adding a measured quantity of energy to the conduit, approximations of the volume of gas and liquid in the system can be made. The final determination of the system composition can be accurately calculated through an iteration process as explained in detail below. In accordance with the invention, the observed data ($F_{Qi}$, $F_{Qo}$, $T_i$, $T_o$, $T_1$, $T_2$, $P_1$, $P_2$ and q) are recorded instantaneously and simultaneously at any point in time. These data and other data and relationships required by the method are used to determine the flows and/or masses of the components as described below.

A completely general solution for either miscible and/or immiscible liquids and a gas is possible and is developed below, wherein:

$F_{Li}$ = flow rate of liquid(s) "in", and $F_{Lo}$ = flow rate of liquid(s) "out".

Then the inlet and outlet flow rates can therefore be expressed as follows:

$F_{Qi} = F_{Li} + V_{gi}$ $F_{Qo} = F_{Lo} + V_{go}$ where $F_{Qi}$ and $F_{Qo}$ are total fluid flows measured at the in and out conditions and $V_{gi}$ and $V_{go}$ are the flow or volume of gas in the fluid measured at the in and out conditions.

If the equation for $F_{Qi}$ is subtracted from the equation for $F_{Qo}$, the result is:

$F_{Qo} - F_{Qi} = V_{go} - V_{gi} + F_{Lo} - F_{Li}$.

At this point, let $\alpha = F_{Lo}/F_{Li}$. Rearranging the expression to isolate $F_{Lo}$ yields the following:

$$F_{Lo} = \alpha(F_{Li}).$$

By substituting this latter expression for $F_{Lo}$ in the previous equation, the equation becomes:

$$F_{Qo} F_{Qi} = V_{go} - V_{gi} + \alpha(F_{Li}) - F_{Li} = V_{go} V_{gi} + (F_{Li})(\alpha - 1)$$

The ideal gas law states that:

$$P_i V_{gi}/T_i = P_o V_{go}/T_o.$$

Rearranging to isolate $V_{go}$ and subtracting $V_{gi}$ from both sides of the equation results in the following:

$$V_{go} - V_{gi} = V_{gi}(P_i T_o/T_i P_o) - V_{gi} = V_{gi}([P_i T_o/T_i P_o] - 1).$$

By substituting this value for $V_{go} - V_{gi}$ in the previous equation, the expression for $F_{Qo} - F_{Qi}$ is as follows:

$$F_{Qo} - F_{Qi} = V_{gi}([P_i T_o/T_i P_o] - 1) + (F_{Li})(\alpha - 1).$$

It will be recalled that $\alpha$ represents the ratio of the flow of the liquid components out of the system to their flow into the system, i.e., $\alpha = F_{Lo}/F_{Li}$. Since neither liquid volumes nor liquid densities change significantly with small changes in temperature, this ratio is approximately equal to unity. If the value of $\alpha$ is first assumed to be 1.0, the expression in the equation dependent on the value of $\alpha$ equals zero, leaving:

$$F_{Qo} - F_{Qi} = V_{gi}([P_i T_o/T_i P_o] - 1).$$

Rearranging the terms to isolate $V_{gi}$ results in the following equation:

$$V_{gi} = (F_{Qo} - F_{Qi})/([P_i T_o/T_i P_o] - 1).$$

Note that all of the terms in the right side of the equation are measured values, allowing the equation to be solved for the first approximation of $V_{gi}$. $V_{go}$ may now be calculated using the ideal gas law equation and the first approximation of $V_{gi}$.

Recalling that $F_{Qi} = F_{Li} + V_{gi}$, this equation can be rearranged as follows:

$$F_{Li} = F_{Qi} - V_{gi}.$$

Using the solved value for the first approximation of $V_{gi}$, and knowing the measured value of $F_{Qi}$, the first approximation for the liquid volume of $F_{Li}$ can be calculated; however, additional data, relationships and calculation procedures as developed below are required to accurately define the stream components ($V_{gi}$, $m_{Ai}$ and $m_{Bi}$).

The relationship of added heat to the specific heat of a fluid, where all process data are recorded instantaneously at the time when a process composition analysis is required, is expressed by the general formula:

$$q = m c_p \Delta t + q' + q''$$

which can also be expressed as $$q = F \rho c_p \Delta t + q' + q''$$

where:
q = heat added to the apparatus, BTU/day,
m = mass flow rate, lbs/day,
F = flow rate, ft³/day
$\rho$ = density at the average investigative conditions, lbs/ft³,
$c_p$ = average specific heat (constant pressure) of the flowing substances at the average investigation temperature and pressure, BTU/lb °F.,
$\Delta t$ = temperature change of the fluid flowing through the conduit due to heat input, q, in °F., ($T_o - T_i$),
q' = heat loss through insulation, BTU/day, ($T_2 - T_1$), and
q'' = heat loss to the apparatus, BTU/day.

This formula can be rewritten for a fluid system comprised of two liquid components (A and B) and a gas component, as follows:

$$q = F_L \rho_L C_{pL} \Delta t + q' + q'' + q'''$$

where:
$F_L$ = average flow rate of the liquid system, ft³/day,
$\rho_L$ = average density of the liquid system, lbs/ft³,
$C_{pL}$ = average specific heat of the liquid system, BTU/lb °F., and
q''' = heat absorbed by the gas phase, BTU/day.

Solving for the product of density and specific heat, and utilizing the terminology of the present example, the formula becomes:

$$\rho_L c_{pL} = (q - q' - q'' - q''')/(T_o - T_i)(F_L).$$

The values of the various heat losses must be determined to solve for $\rho_L c_{pL}$.

The rate of heat loss to the apparatus at the instant a data point is taken equals zero assuming the apparatus is at equilibrium with its environment. Therefore, by running the apparatus so that q'' = 0, this item in the equation can be dropped.

As to the heat loss through the insulation, q', if the insulation properties are known in sufficient detail, the heat loss can be calculated using the following equation:

$$q' = k A_m \Delta t'$$

where:
k = thermal conductivity of insulation, BTU/hr°Fft,
$A_m$ = mean area of insulation for heat loss, ft², and
$\Delta t'$ = temperature difference between inside and outside insulation surfaces, °F. (i.e. $T_2 - T_1$).

While such a calculation satisfactorily determines the heat loss from the apparatus, it is preferred to run water through the apparatus and to calculate the heat loss from measurements of the flow rate and of the temperature difference between the inside and outside insulation surfaces as a result of varying the energy input. Since the specific heat and density for water are known in great detail and accuracy, the heat loss, q', can be calculated very accurately by means of the general equation of heat loss, modified for the condition where q'' = 0, as follows:

$$q = m c_p \Delta t + q'.$$

To utilize the measurement of volumetric flow rate, the mass flow rate, m, is replaced with its equivalent volumetric term, $F_Q \rho_Q$, where $F_Q$ = flow rate in cubic feet per day (ft³/day) and $P_Q$=density in pounds per cubic foot (lbs/ft³). Converting to consistent units results in the expression:

$$q = F_Q \rho_Q c_{pQ} \Delta t + q' \qquad 5$$

where the subscript Q refers to the entire stream average properties.

The heat added, q, can be expressed in terms of the electric power added to the system, which can be determined through the general equation:

$$W = EI = E^2/R$$

where:
- W = electric power added to the system, watt hrs,
- E = applied power, volts, and
- R = electrical resistance of conduit heater, ohms.

Knowing that 3.413 BTU equals one watt hour, the heat added may be expressed in terms of the power input to the fluid by converting BTU's/day to watt hrs/day, whereby q=3.413 W. By substituting this value for q, the equation for heat added becomes:

$$3.413\, W = F_Q \rho_Q c_{pQ} \Delta t + q'.$$

By expressing power W, in terms of $E^2/R$ the equation becomes:

$$3.413 E^2/R = F_Q \rho_Q c_{pQ} \Delta t + q'$$

or $$E^2/R = W = 0.2933\, F_Q \rho_Q c_{pQ} \Delta t + q'/3.413.$$

With water as the fluid and under given operating conditions, every variable in this equation is known except q'. Thus q' can be algebraically determined by means of a simple, direct calculation.

Figure 2:
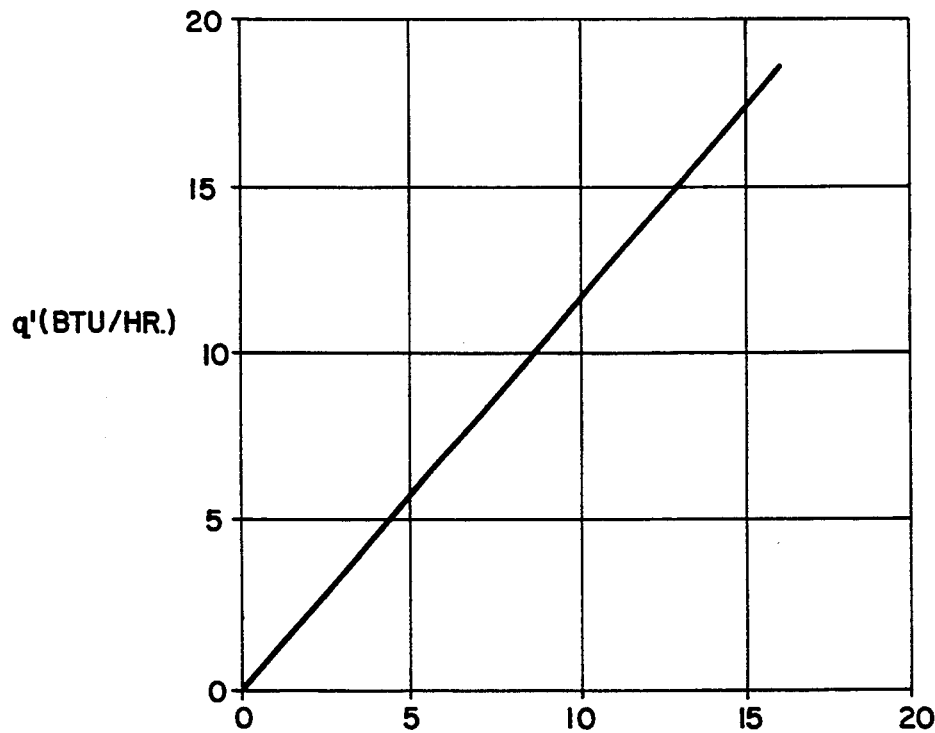
FIG. 2 is a graph showing the relationship between the temperature differential of the inner and outer surfaces of the conduit insulation and the heat loss of the system.

Going back to the equation for heat loss, $q' = kA_m \Delta t'$, and recalling that $\Delta t'$=the temperature difference between the inside and outside insulation surfaces $(T_2-T_1)$, it can be seen that q' is linearly related to $T_2-T_1$ inasmuch as k and $A_m$ are constants for any given apparatus. Thus, if the values of $T_1$ and $T_2$ are noted at the time the data for calculating q' is collected, the relationship between heat loss, q', and $T_2-T_1$ can be plotted. By changing the level of power input or flow rate, additional values for q' and $T_2-T_1$ are generated. These values can be used to plot $T_2-T_1$ against q' to produce a graph of the type shown in FIG. 2. It will be appreciated that the slope of the linear curve should be $kA_m$, which is a fixed number based on the design of the apparatus and which passes through the origin (0,0) of the coordinates. Therefore, although data may be collected to provide more than one point on the graph, only a single point is required in order to draw the graph.

The relationship between q' and $T_2-T_1$ depends on the instrument design but is independent of the fluid being evaluated. Therefore, the heat loss for any fluid flowing through the apparatus can be accurately determined by measuring $T_2-T_1$ and reading the heat loss, q', from the graph. If desired, a quick and accurate check on the system operation and on all the measuring devices can be made by running the apparatus on water prior to running the unknown fluid.

The value of the heat absorbed by the gas phase can be calculated by using the first approximation of $V_{gi}$, the gas density $\rho_g$, and the gas specific heat $c_{pg}$ in the equation:

$$q''' = (V_g \rho_g c_{pg})(T_o - T_i)$$

where $V_g = (V_{gi} + V_{go})/2$.

The data for the specific heat and density of the gas component may be obtained from various sources, such as textbooks, handbooks, instrument supplier data and chemical manufacturer data. Since it is unlikely, however, that all the necessary data is available at the desired investigation temperature and pressure, it may be necessary to develop the data at the desired investigation temperature and pressure by means of the apparatus described above. Enough data should be taken to enable a smooth curve to be drawn through the data points for the concentrations in the area of interest.

Returning to the formula:

$$\rho_L c_{pL} = (q - q' - q'' - q''')/(T_o - T_i)(F_L),$$

it can be seen that $T_o - T_i$ is a measured value, $F_L$ has a first approximated value, and the values for heat losses q', q'', and q''' are obtained as explained above. Since q is also a measured number, all values on the right hand side of the equation are known or approximated and $\rho_L c_{pL}$ can now be readily calculated. As stated previously, q=3.413 W, where W is power added in terms of watt hours. Converting to a 24-hour day basis to be consistent with the measured flow terms, the value for q would be 81.89 W.

Figure 3:
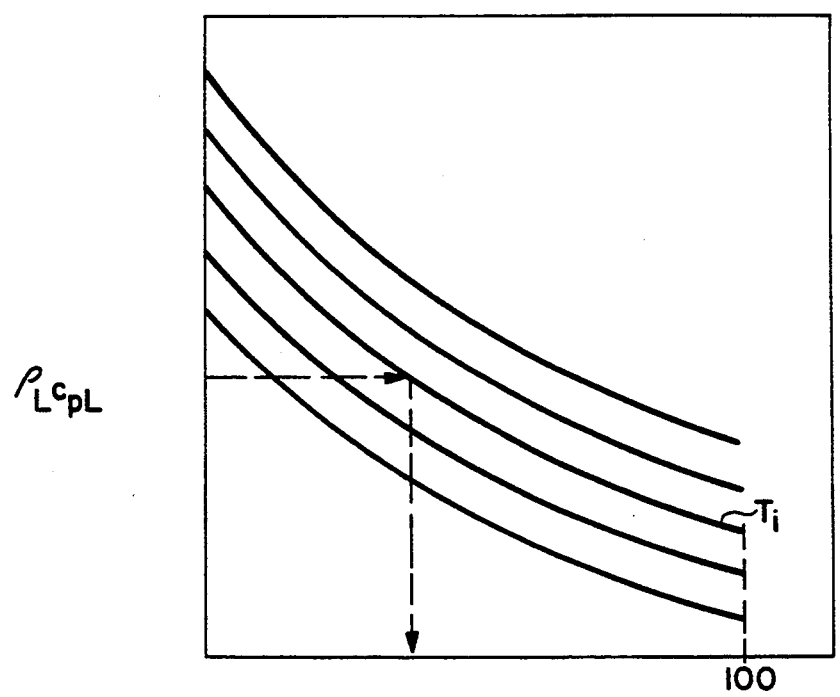
FIG. 3 is a graph illustrating the relationship between the product of the density and specific heat as a function of the liquid mass composition in a two-component liquid mixture.

As shown in FIG. 3, when the relationship of $\rho_L c_{pL}$ to the mass fraction of A in the mix A+B is plotted at various temperatures the first approximation of mass fraction of liquid A and liquid B can be determined from the graph, and remembering that A+B=100%, $m_A$ and $m_B$ can then be calculated from $m_A = Am_L$ and $m_B = Bm_L$.

Figure 4:
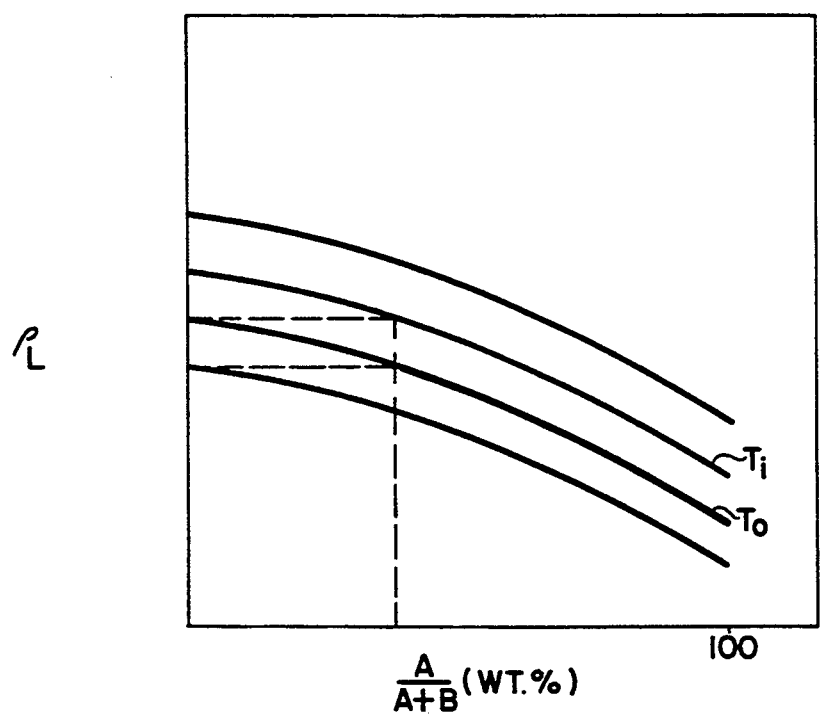
FIG. 4 is a graph illustrating the relationship between the liquid density and the mass composition at various temperatures for the liquid system.

Since the temperatures $T_i$ to $T_o$ are measured values, and the average liquid density as a function of A/A+B at various temperatures is known, as graphically illustrated in FIG. 4, $\rho_{Li}$ and $\rho_{Lo}$ can be determined and a second approximation of $\alpha$ can be calculated from the relationship $\alpha = \rho_{Li}/\pi_{Lo}$. The second approximate value of $\alpha$ and the first approximate value of $F_{Li}$ can now be substituted in the previous equation:

$$F_{Qo} - F_{Qi} = V_{gi}\{[P_i T_o/T_i P_o] - 1\} + (F_{Li})(\alpha - 1)$$

and the equation solved for a second approximation of $V_{gi}$. Repeating the steps previously outlined permits calculation of approximate stream composition and a third approximate $\alpha$. Using this approximate e value, a third approximation of $V_{gi}$ is calculated, followed by a third approximation of $F_{Li}$. These steps, which constitute an iteration process, are repeated until the last computed value of e equals the previous $\alpha$, the last computed value of $V_{gi}$ equals the previous value and the last computed value of $F_{Li}$ equals the previous value, thus accurately defining the components $A_i$, $B_i$ and $V_{gi}$ of the fluid composition.

It should be noted that instantaneous measurements for simplicity have been used to illustrate the method. The average composition for any time frame can be obtained by summing these instantaneous compositions over the desired time frame.

It will be apparent to those skilled in the art that one immiscible liquid may be replaced with an immiscible solid or both liquids by two solids and further that the apparatus must be designed and operated so as to essentially eliminate any work caused by expansion or contraction of the gas as it passes through the conduit.

As illustrated in FIG. 1, a programmable logic controller 58 is provided to which the input measurements are directed. In view of the complex iteration process employed, the need for a computer to gather data, to store necessary relationships and data and to timely compute the results is obvious.

Although the energy added to induce meaningful changes between inlet and outlet conditions enabling the stream composition to be calculated could be heat or pressure, it is preferred to use heat because of the simplicity of the process and of the necessary equipment.

As noted, the conduit employed in the apparatus used to generate the data discussed above was formed from NICHROME alloy. While the invention is not limited to use of such material, there are nonetheless certain parameters that the material should meet. The material from which the conduit is formed, whether it is a metal alloy or a nonmetal such as carbon, needs to be resistant to corrosion from the fluids being evaluated. Further, the temperature coefficient of resistivity for the material needs to be very low so that the electrical resistance of the conduit is essentially constant over the expected operating temperature range. In addition, the electrical resistance of the conduit needs to be high enough to be easily and accurately measured, as does the operating voltage. For example, a copper tube having the same dimensions as the NICHROME tube previously described would have an electrical resistance of about 0.0077 ohm, and thus require only 0.77 applied volts to put out 100 watts, as compared to 0.45 ohm and 6.71 applied volts for the NICHROME conduit. The 0.0077 ohm resistance, in particular, is very difficult to measure accurately. Since the electrical resistance of the conduit is a function of the length and cross-sectional area of the conduit and the electrical resistivity of the material from which the conduit is formed, a desired value of electrical resistance can be designed into the conduit. For the purpose of easily and accurately measuring the electrical resistance of the conduit and the operating voltage, the electrical resistance should be at least 0.3 ohm and the operating voltage in the range of 5–24 volts.

On the other hand, it is not desirable to utilize a conduit formed from a material having very high electrical resistance since such a conduit could force enough power through a conductive fluid to give significant, but hard to measure, power and hence produce erroneous results. For the particular condition where one is looking at very high water contents, such as, for example, 99%, the electrical resistance of the conduit should be no more than about 0.0005 times the electrical resistance of the fluid. The apparatus of the invention described previously, for example, has an electrical resistance of about 0.0002 times that of a 28% sodium chloride brine. Thus the apparatus meets this criteria even for a highly conductive brine.

If it is not desirable for the conduit to be in contact with the fluid being examined, the conduit could be coated or lined with electrically insulating material. Further, it is not necessary that direct current be used to power the apparatus. Alternating current will work as well.

The heater used to heat the fluid flowing through the conduit 12 of FIG. 1 may be of any suitable design which is sensitive to slight changes in power input. For example, the conduit may be covered with an electrical insulator, which is then wrapped with a high resistivity wire or ribbon, which in turn is then covered with another electrically insulating material. Some commercially available heaters which operate in a similar fashion are comprised of foil material having a high resistivity laminated between two thin sheets of polymeric material having high electrical resistance. While these heater designs function adequately, it is nevertheless preferred to use a conduit such as the one described in connection with FIG. 1 which has a high electrical resistance so that it can serve as the electrical heater.

There are several reasons why this is preferred. Since the entire conduit between the electric terminals is available for heat transfer, the area of the conduit so available is the largest theoretically possible and is used anytime current is applied. Further, there is no more efficient way to add heat to the flowing fluid due to the fact that the overall heat transfer coefficient will be higher when the conduit is used as the heater because there are fewer heat transfer barriers in such an arrangement. Due to these features, the combination conduit-heater will have a lower temperature for a given area and will therefore not be as susceptible to failure from burn-out or hot spots. It will also have less heat loss so that the same percent error in the heat loss measurement will be a lower number and produce less error in the final measurement. In addition, the dual use of the conduit allows the apparatus to be used in higher temperature applications and minimizes the size of the conduit in view of the fact that no temperature sensitive electrical insulating materials are required between the heater and the conduit. Response is also improved as the mass of the instrument is minimized.

The composition analyzer is comprised of readily available components and the necessary measurements can be made by standard measuring instruments. The invention may be used wherever the composition of a three-part multiphase fluid system is desired to be known, one practical application out of many being to measure the oil/water/gas composition of fluid produced from a hydrocarbon formation. In such an application, and in others, the invention readily lends itself to use in the field, since the size of the apparatus is small and the required energy input can be from a small generator or battery.

It will be apparent that the invention need not necessarily be limited to all the specific details described in connection with the preferred embodiment, except as such details may be required by the appended claims, and that changes to certain features of the preferred embodiment which do not alter the overall basic function and concept of the invention are contemplated.

What is claimed is:

1. A composition analyzer for determining the composition and flow rate of a multicomponent, multiphase fluid containing a gas, comprising:

a conduit permitting a multicomponent, multiphase fluid to flow therethrough;

means for heating a section of the conduit;

thermal insulation covering the heated section of the conduit;

means for measuring the temperature, pressure and flow rate of the fluid at points closely adjacent to, and upstream and downstream from, the heated section of the conduit;

means for measuring the temperatures at the inside and outside surfaces of the insulation to enable the temperature differential therebetween to be determined;

a programmable logic computer to which measurements of temperature, pressure, flow rate and energy applied by the heating means are sent, the computer being programmed to:

determine the approximate volume of the gas in the multiphase fluid through use of the ideal gas law based on a first assumption that the ratio of the volume of the liquid components flowing into the conduit section to the volume of the liquid components flowing out of the conduit section is equal to one;

determine the approximate liquid volume of the multiphase fluid based on the approximate volume of gas determined to be in the multiphase fluid and on the measured flow rate of the multiphase fluid upstream of the heated section of the conduit;

determine the heat absorbed by the gas through calculations utilizing the approximate volume of gas determined to be in the fluid, the density and specific heat of the gas and the aforesaid temperature differential;

determine the heat lost through the conduit insulation to the ambient environment through calculations utilizing the thermal conductivity of the insulation, the aforesaid temperature differential and the mean area of insulation involved, or through calculations based on the aforesaid temperature differential, the amount of heat added to the conduit section and the flow rate and specific heat of the fluid;

determine the product of the density and specific heat of the liquid in the fluid based on the amount of heat added to the fluid, the amount of heat absorbed by the gas, the amount of heat lost through the conduit insulation, the difference in temperature of the fluid upstream and downstream of the heated section of the conduit and the flow rate of the liquid; and determine an approximation of the volume of each liquid component in the approximated liquid volume of the fluid, as determined from a known relationship between the product of the specific heat and density of the liquid components and the mass ratio of the specific heat and density to the liquid components.

2. The composition analyzer of claim 1, wherein the programmable logic computer is programmed to:

calculate a new ratio of the volume of the liquid components flowing into the conduit section to the volume of the liquid components flowing out of the conduit section based on the aforesaid calculated values; and repeat the calculation process until the last computed ratios equal the previous computed ratios.

3. The composition analyzer of claim 1, wherein the means for heating a section of the conduit comprises:

an electrical resistance heater; and the electrical resistance heater including means for applying electrical energy and measuring the amount of electrical energy applied to the insulated section of the conduit to raise the temperature of said section and thus heat fluid flowing therethrough.

4. The composition analyzer of claim 3, wherein the conduit is comprised of electrically conductive material having an electrical resistance such that the material functions as a heater when electrical enemy is added thereto, the electrically conductive material of the conduit having an electrical resistance of at least 0.3 ohm and an electrical resistance which is not greater than about 0.0005 times the electrical resistance of the multiphase fluid.

5. The composition analyzer of claim 4, wherein the conduit is comprised of an alloy of nickel, chromium and iron.

* * * * *

UNITED STATES PATENT AND TRADEMARK OFFICE
CERTIFICATE OF CORRECTION

PATENT NO. : 5,415,024
DATED : May 16, 1995
INVENTOR(S) : Arthur C. Proffitt and William C. Barron It is certified that error appears in the above-indentified patent and that said Letters Patent is hereby corrected as shown below:

Col. 5, line 10: Delete "$F_{oo}F_{oi}=V_{go}-V_{gi}+a(F_{Li})-F_{Li}=V_{go}V_{gi}+(F_{Li})-$" and insert --$F_{oo} - F_{oi} = V_{go} - V_{gi} + a(F_{Li}) - F_{Li}$--

Col. 5, line 11: Delete "(a-1)" and insert --$= V_{go} - V_{gi} + (F_{Li})(a-1)$--.

Col. 8, line 44: Delete "$\alpha = \rho_{Li} / \pi_{Lo}$" and insert --$\alpha = \rho_{Li} / \rho_{Lo}$--.

Col. 8, line 53: Delete "Using this approximate e value," and insert "Using this approximate $\alpha$ value,--.

Col. 8, line 57: Delete "value of e equals" and insert --value of $\alpha$ equals--.

Signed and Sealed this

Nineteenth Day of September, 1995

Attest:

BRUCE LEHMAN

*Attesting Officer*          *Commissioner of Patents and Trademarks*